(12) United States Patent
Kramer et al.

(10) Patent No.: US 11,255,723 B2
(45) Date of Patent: Feb. 22, 2022

(54) BEAM POWER MEASUREMENT WITH WIDENING

(71) Applicant: PRIMES GMBH, Pfungstadt (DE)

(72) Inventors: Reinhard Kramer, Pfungstadt (DE); Otto Märten, Dreieich (DE); Stefan Wolf, Groß-Gerau (DE); Roman Niedrig, Berlin (DE)

(73) Assignee: PRIMES GMBH, Pfungstadt (DE)

( * ) Notice: Subject to any disclaimer, the term of this patent is extended or adjusted under 35 U.S.C. 154(b) by 255 days.

(21) Appl. No.: 16/321,016

(22) PCT Filed: Jul. 11, 2017

(86) PCT No.: PCT/DE2017/000205
§ 371 (c)(1),
(2) Date: Jan. 26, 2019

(87) PCT Pub. No.: WO2018/024268
PCT Pub. Date: Feb. 8, 2018

(65) Prior Publication Data
US 2020/0025608 A1    Jan. 23, 2020

(30) Foreign Application Priority Data
Aug. 5, 2016  (DE) .......................... 102016009475.3

(51) Int. Cl.
*G01J 1/42*     (2006.01)
*G01J 1/04*     (2006.01)

(52) U.S. Cl.
CPC .......... *G01J 1/4257* (2013.01); *G01J 1/0403* (2013.01); *G01J 1/0411* (2013.01); *G01J 1/0414* (2013.01); *G01J 1/0474* (2013.01)

(58) Field of Classification Search
CPC ...... G01J 1/4257; G01J 1/0403; G01J 1/0411; G01J 1/0414
See application file for complete search history.

(56) References Cited

U.S. PATENT DOCUMENTS 3,687,558 A    8/1972  Rex
4,346,970 A *  8/1982  Kawabata ............. G02B 7/346
                                            396/113
(Continued)

FOREIGN PATENT DOCUMENTS

CN    101285712 A    10/2008
CN    103389157 A    11/2013
(Continued)

OTHER PUBLICATIONS

English Translation of Abstract of Japanese Patent Application No. JP S59-44628 dated Jan. 23, 2019.
(Continued)

*Primary Examiner* — Que Tan Le
*Assistant Examiner* — Don J Williams
(74) *Attorney, Agent, or Firm* — McDonnell Boehnen Hulbert & Berghoff LLP

(57) ABSTRACT

The invention relates to a method and an apparatus for the direct and precise measurement of the power and/or energy of a laser beam, which make a measurement possible even in areas close to the focus of a laser beam, A device is proposed for this purpose that contains a radiation sensor, an expansion device, and a support mount. The radiation sensor has a receiving surface and is configured for the generation of an electrical signal, which is dependent on the power of the laser beam or the energy of the laser beam. The expansion device and the radiation sensor are positioned on the support mount at a distance from one another. The expansion device is configured in such a way as to increase the angle range of the laser beam. The laser beam propagates to the radiation sensor with an increased angle range. A diameter of the laser beam propagated on the receiving surface is greater than a diameter of the laser beam in the area of the expansion device. The receiving surface of the radiation (Continued)

sensor encloses at least 90% of the cross-section surface of the laser beam propagated.

20 Claims, 13 Drawing Sheets

(56) References Cited

U.S. PATENT DOCUMENTS

| | | | |
|---|---|---|---|
| 5,678,924 | A | 10/1997 | Naquin et al. |
| 5,805,277 | A * | 9/1998 | Kruger .................. G01J 1/0474 356/213 |
| 5,936,720 | A | 8/1999 | Neal et al. |
| 6,072,573 | A | 6/2000 | Kruger et al. |
| 7,077,564 | B2 | 7/2006 | Schloss et al. |
| 2003/0012252 | A1 | 1/2003 | Bender |
| 2003/0099276 | A1 | 5/2003 | Argenti |
| 2005/0270543 | A1 * | 12/2005 | Ge ........................ G01J 1/4257 356/512 |
| 2010/0253937 | A1 * | 10/2010 | Zerl ...................... G01J 1/0448 356/122 |
| 2013/0001605 | A1 | 1/2013 | Ishihara et al. |
| 2015/0129750 | A1 | 5/2015 | Nikrin et al. |

FOREIGN PATENT DOCUMENTS

| | | |
|---|---|---|
| DE | 3919571 A1 | 12/1990 |
| DE | 4336589 C1 | 12/1994 |
| DE | 10012536 A1 | 9/2000 |
| DE | 10253905 A1 | 6/2003 |
| DE | 102012106779 A1 | 1/2014 |
| DE | 102014012913 A1 | 3/2016 |
| EP | 0629845 A1 | 12/1994 |
| GB | 2347998 A | 9/2000 |
| JP | S59-44628 A | 3/1984 |
| JP | 04-066541 U | 6/1992 |
| JP | 07-174620 A | 7/1995 |
| JP | 2013-016586 A | 1/2013 |
| WO | 9721989 A1 | 6/1997 |
| WO | 2010125344 A1 | 11/2010 |
| WO | 2014/050859 A1 | 4/2014 |

OTHER PUBLICATIONS

English Translation of Abstract of German Patent Application No. 39 19 571 dated Jan. 24, 2019.

English Translation of Abstract of German Patent Application No. 43 36 589 dated Jan. 24, 2019.

English Translation of Abstract of German Patent Application No. 10 2012 106 779 dated Jan. 24, 2019.

English Translation of Abstract of German Patent Application No. 10 2014 012 913 dated Jan. 24, 2019.

Japanese Office Action for JP Application No. 2019-506116, dated Feb. 2, 2021.

* cited by examiner

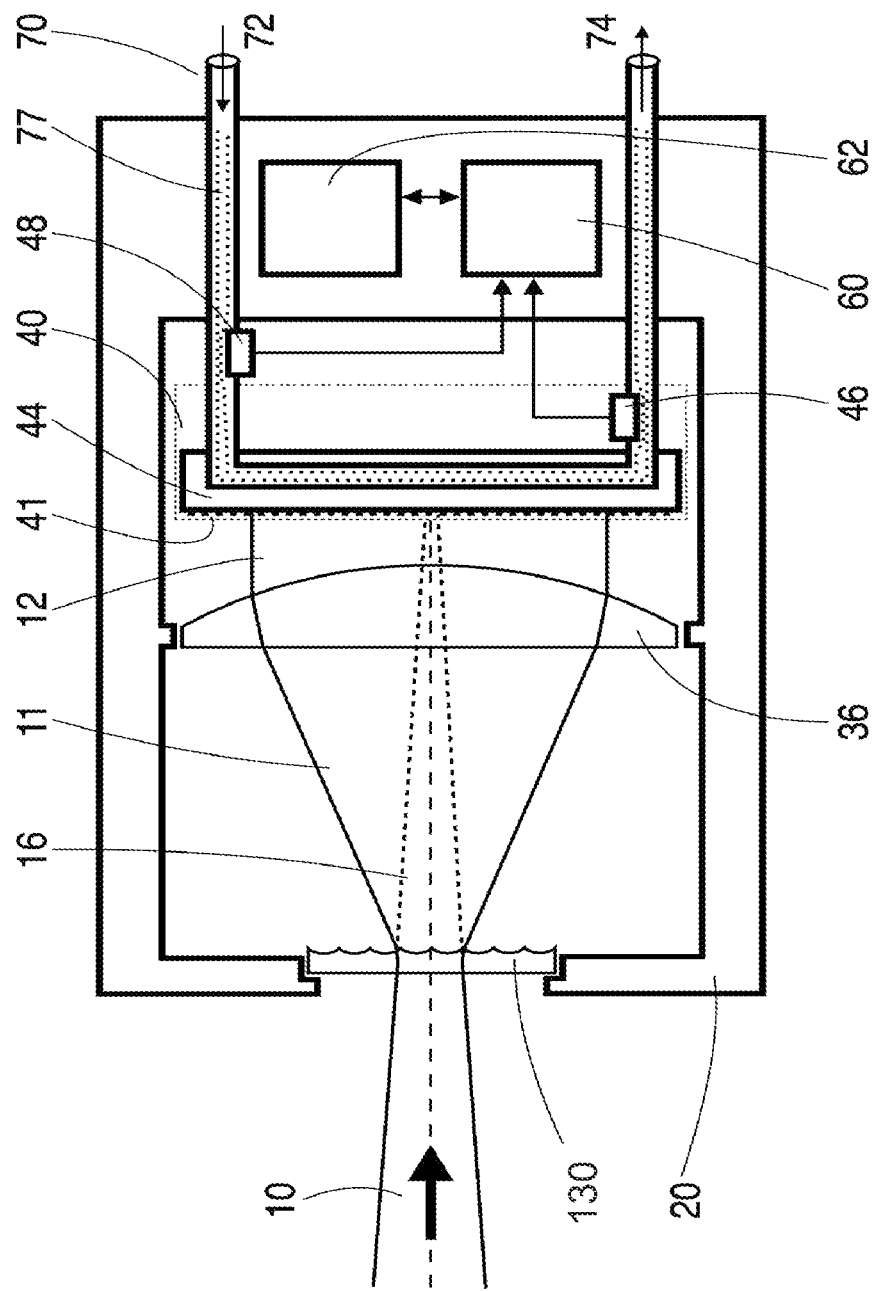

BEAM POWER MEASUREMENT WITH WIDENING

CROSS REFERENCE TO RELATED APPLICATIONS

The present application is a U.S. National Phase Application pursuant to 35 U.S.C. § 371 of International Application No. PCT/DE2017/000205 filed Jul. 11, 2017, which claims priority to German Patent Application No. 10 2016 009 475.3 filed Aug. 5, 2016. The entire disclosure contents of these applications are hereby incorporated by reference into the present application.

FIELD OF THE INVENTION

The invention relates to a method and an apparatus for the measurement of the power or the energy of a laser beam. The invention makes possible the direct measurement of laser radiation with very high power density, such as of focused laser beams in the region of laser beam focus, for example.

BACKGROUND OF THE INVENTION

Devices for the measurement of the energy or the power of a laser beam are known in great numbers and with different operating principles. One possibility for the measurement of the power or energy of a laser beam is the use of a photodiode. Reference is made, by way of example, to the U.S. Pat. No. 3,687,558, in which a laser power energy measuring device with a photodiode and an electronic circuit is disclosed. Such types of devices are suitable, in particular, for the measurement low radiant powers. At higher power densities, a photodiode can rapidly be saturated or even destroyed.

In the case of higher beam powers, measurements are thus generally carried out indirectly, i.e., the beam does not impinge on the detector directly, or not with its entire cross-section, One possibility for indirect measurement consists, first of all, of the attenuation of the laser beam, as is shown in DE 100 12 536 A1, for example. In the device for the measurement of the intensity of a light beam proposed there, a light-absorbing window and a device for scattering and attenuation of the light are placed in front of the detector. Since the detector here measures only a small portion of the light irradiated, greater effort must be made in order to keep the sensitivity of the value of the position and the angle of the light beam detected on the light-absorbing window slight. In addition, the attenuated beam power is primarily converted into heat, which can adversely affect the precision, since the sensitivity of semiconductor sensors is generally dependent on temperature, such as because of temperature-dependent dark current, for example.

One additional common method for indirect measurement is the decoupling of a small portion of the beam for measurement. A device of this type is presented in DE 43 36 589 C1. A laser power measuring device, in which a high-transmitting beam splitter reflects a fraction of the laser beam to the sensor, is disclosed there. The dependence of the degree of reflection on the polarization and the angle of incidence of the laser beam is here problematic, so that calibration, and thereby a precise measurement, are difficult. For the solution of the problem of polarization-dependence, it is proposed, in a second embodiment of DE 43 36 589 C1, to position two beam splitters of the same specification in succession, wherein the second deflection takes place in a plane perpendicular to the first deflection. The problem of angle dependence still persists, however, for which reason the device is only suitable for collimated radiation and must be aligned precisely.

DE 10 2012 106 779 B4 depicts a further developed device of a similar type with several reflections in various planes. In the optics for beam measurement disclosed there, three partially-reflecting mirrors are used, in order to compensate for the polarization dependence and, in addition, to compensate for the angle dependence of the reflection, so that a measurement is possible, even under divergent radiation. The device disclosed there, however, is primarily provided for the measurement of geometrical beam data, that is to say, for the measurement of intensity profiles and for the determination of beam parameters, and is less suitable for the determination of the total power of a beam.

A measurement of total radiant power with devices in which the beam is strongly attenuated is always limited in its precision. On the one hand, a complex calibration which restricts the measuring accuracy is necessary and, on the other hand, even small parameter deviations in the elements involved can influence the attenuation factor and can, because of the high attenuation factor, lead to considerable changes in the sensitivity of the measuring device.

Direct measuring methods can thus be advantageous in regard to the achievable precision. High precisions are achievable with calorimetrical methods, in which the laser radiation impinging on a detector is essentially converted into heat and the temperature changes, the temperature gradients forming or the heat flows dissipated can be measured. Even very high powers can thereby be measured, in principle, if sufficient cooling of the detector is provided. Thus, for example, in DE 10 2014 012 913 A1 an energy beam power measurement is disclosed in which the energy radiation is absorbed by an absorber and the absorber is cooled by means of a stationary fluid flow. The beam power is determined from the temperature increase in the cooling fluid by comparison with a temperature increase of the fluid by means of electrical heating. Very high powers can thereby be measured, but the power must be distributed within the absorber, in order for no local overheating and possible damage of the absorber to take place. A measurement in the region of a beam focus is thus not possible.

U.S. Pat. No. 5,678,924 depicts an example of a laser power measuring device with an air-cooled measuring head. The measuring head contains a target disk in thermal contact with a heat sink. Upon the irradiation of the target disk, a temperature gradient forms in the target disk, which is determined with an arrangement of thermoelements. Because of the heat sink and the air cooling with ventilators, the measuring head arrangement is constructed relatively large, so that an application is difficult upon limited space conditions. Upon an application in the region of a beam focus, the target disk can overheat locally and be damaged.

Calorimetrical measuring devices can be constructed significantly compactly, if operating in accordance with the ballistic principle. An active cooling is omitted here and the measurement is limited to a short time period. The energy or power can be determined from the temperature increase of the target body or the absorber. Patents DE 102 53 905 A1 and the U.S. Pat. No. 7,077,564 B2 depict typical representatives of such a class of measuring device. Since the beam here impinges directly on the absorber, a measurement of laser radiation with high power is not possible in the region of a beam focus, since the absorber can be damaged in spots through overheating.

Upon the direct measurement of laser radiation with high power or high power density, therefore, the problem that the device or the sensor can be damaged is generally present. In practically all known measuring devices, care must therefore be taken that the laser beam does not exceed a specific power density on the detector. To this end, the laser beam must have a certain minimum diameter, the value of which is dependent on the damage threshold of the detector and on the power of the laser beam, among other points. For this purpose, the measuring device is usually positioned in the divergent beam at a sufficiently great distance from a beam focus. This is often possible during measurements on experimental constructions in a laboratory, or is at least achievable through partial changes in the set-up.

One important application of laser power measuring devices is the set-up and testing or monitoring of the power or energy of a laser beam in laser material processing plants at regular intervals. The power or energy of the beam at the processing location, where the beam is mostly focused and, as a result, particularly high power densities appear, is of interest here. Therefore, no measurement is thereby possible with common commercial measuring heads at this point; other measuring positions, on which the laser beam is enlarged to a sufficient diameter due to its divergence, are frequently not accessible in laser material processing devices.

A need consequently exists for simple, compact laser power measuring devices that make possible the direct and precise measurement of the power and/or of the energy of a laser beam, even in regions close to the beam focus.

BRIEF DESCRIPTION OF THE INVENTION

The task of this invention is to make available a method and an apparatus for the determination of the power and/or of the energy of a laser beam which are suitable for direct and precise measurements, even in the focus region of a laser beam.

For the solution of the task, an apparatus is proposed for the measurement of the power and/or of the energy of a laser beam, which contains a radiation sensor, an expansion device, and a support mount. The radiation sensor has a receiving surface and is configured for the generation of an electrical signal, which is dependent on the power of the laser beam or the energy of the laser beam. The expansion device and the radiation sensor are positioned on the support mount at a distance from one another, so that the laser beam propagates between the expansion device and the radiation sensors. The expansion device is configured in such a way as to increase the angle range of the laser beam. A diameter of the laser beam propagated on the receiving surface of the radiation sensor is greater than a diameter of the laser beam in the area of the expansion device. Furthermore, the receiving surface of the radiation sensor encloses at least 90% of the cross-section surface of the laser beam propagated.

An embodiment of the apparatus is provided, in which the expansion device is a diverging lens or a converging lens.

The expansion device may also be a plurality of microlenses, referred to in the art as lenslets or an array of microlenses, referred to in the art as a lenslet array.

In one possible embodiment, the expansion device has a light-scattering structure or a light-diffracting structure.

The expansion device can also be a convex mirror, a concave mirror, or a segmented mirror.

In a further possible embodiment, the support mount is configured as a casing that encloses the expansion device and the radiation sensor and has an opening toward the expansion device.

The radiation sensor can be configured in such a way that an intensity locally varying within a cross-section of the laser beam is measured as an integral value.

The radiation sensor can be a large-area photodiode, a large-area semiconductor sensor, a pyroelectrical detector, a thermopile, or a pyrometer.

In a possible embodiment of the apparatus, the radiation sensor comprises an absorption body and a temperature sensor. The temperature sensor is thermally coupled with the absorption body.

A possible embodiment is also provided, in which the apparatus contains a light sensor which is configured for the detection of a slight portion of the laser beam or of a scattered light portion of the laser beam.

In a further possible embodiment of the apparatus, a collimation device can be positioned between the expansion device and the radiation sensor.

The collimation device may comprise a converging lens, an optics consisting of several lenses, a Fresnel lens, a gradient index lens, or a concave mirror.

In yet another possible embodiment of the apparatus, a beam guiding device can be positioned between the expansion device and the radiation sensor.

The beam guiding device can be a light-conducting prism, an inner cylinder mirror, an inner cone mirror, or a kaleidoscope-like mirror arrangement.

There is also proposed for the solution of the task a method for the measurement of the power and/or of the energy of a laser beam with the following method steps. The angle range of the laser beam is increased by means of an expansion device. The laser beam propagates from the expansion device to a radiation sensor with a receiving surface, wherein the expansion device and the radiation sensor are positioned on a support mount at a distance from one another. At least 90% of the cross-section surface of the laser beam propagated is measured by means of the receiving surface of the radiation sensor, wherein a diameter of the laser beam propagated on the receiving surface is greater than a diameter of the laser beam in the area of the expansion device. An electrical signal is generated by means of the radiation sensor in dependence on the power of the laser beam or the energy of the laser beam.

A method is also provided in which the increase of the angle range of the laser beam is carried out by means of a diverging lens, a converging lens, a lens array, a microlens array a lenslet array), a light-scattering structure, a light-diffracting structure, a convex mirror, a concave mirror, or a segmented mirror.

In one possible method, an intensity locally varying within a cross-section of the laser beam is measured as an integral value.

A method is additionally provided in which the radiation sensor contains an absorption body and a temperature sensor. The measuring of at least 90% of the cross-section surface of the laser beam by the receiving surface of the radiation sensor takes place through the absorption of the primary portion of the laser beam impinging on the receiving surface by means of the absorption body. The production of the electrical signal in dependence on the power or energy of the laser beam takes place through the temperature sensor, which is thermally coupled with the absorption body.

It is provided in a further possible method to determine an energy or power of the laser beam from the difference in the temperatures of the absorption body after the end of the irradiating of the laser beam and before the beginning of the irradiating of the laser beam.

An additional method step can also be provided by measuring a slight portion of the laser beam or a scattered light portion of the laser beam by means of a light sensor.

A possible method which contains the following additional method step is also provided. The energy of the laser beam is determined from the difference in the temperatures of the absorption body after the end of the irradiation of the laser beam and before the beginning of the irradiation of the laser beam. An irradiation period of the laser beam is determined from the course of the signal of the light sensor. The power of the laser beam is, finally, determined through the division of the energy and the irradiation period.

In a further possible method, the propagation of the laser beam from the expansion device to the radiation sensor can take place in two sections. The angle range of the propagating laser beams between the two sections is reduced by means of a collimation device, which is positioned between the expansion device and the radiation sensor.

A method is also provided in which the propagated laser beam is centered on the receiving surface of the radiation sensor by means of a beam guiding device, which is positioned between the expansion device and the radiation sensor.

BRIEF DESCRIPTION OF THE FIGURES

The invention is depicted in further detail by means of the following figures, without being restricted to the embodiments and examples depicted. On the contrary, embodiments are also provided in which several characteristics depicted in different can be combined. These depict the following:

FIG. 17: A representation of an additional example of implementation of the second embodiment of the invention, in which the radiation sensor is equipped with a cooling device.

DETAILED DESCRIPTION OF THE FIGURES

Figure 1:
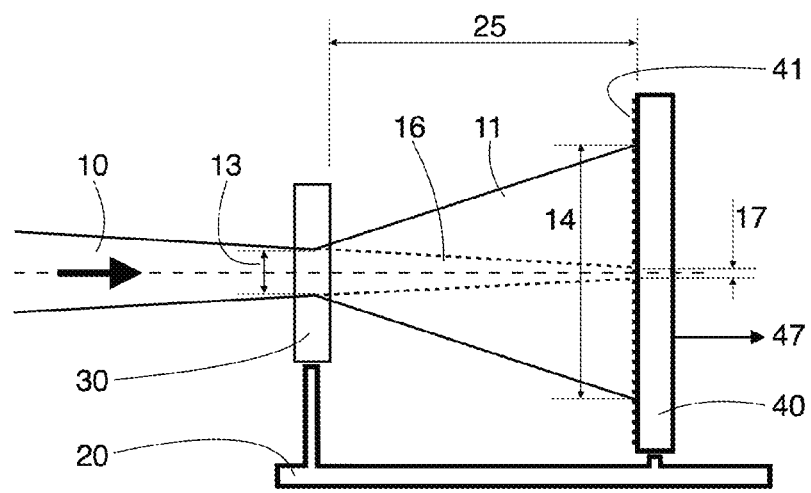
FIG. 1: A schematic representation of a first embodiment of the invention with an expansion device and a radiation sensor.

FIG. 1 depicts a first possible embodiment of the invention in a schematic representation. For the measurement of the energy or the power of a laser beam 10, a radiation sensor 40 is provided with a receiving surface 41. An expansion device 30 is positioned at a distance 25 in front of the radiation sensor 40. The expansion device 30 and the radiation sensor 40 are attached to a support mount 20. The expansion device 30 increases the angle range of the laser beam 10. After passing the expansion device 30, the laser beam 11 propagates with an expanded beam cross-section and impinges with a diameter 14 on the receiving surface 41 of the radiation sensor 40. The receiving surface 41 receives at least 90% of the cross-section of the laser beam propagated 11. The diameter 14 of the laser beam 11 on the receiving surface 41 is here larger than the diameter 13 of the laser beam 10 in the area of the expansion device 30. Without the expansion device 30, the laser beam 16 would not increase in the cross-section and would thus have a very small diameter 17 in the area of the radiation sensor 40. The radiation sensor 40 generates an electrical signal 47, which is dependent on the energy of the power of the laser beam 10 or of the laser beam propagated 11.

Figure 2:
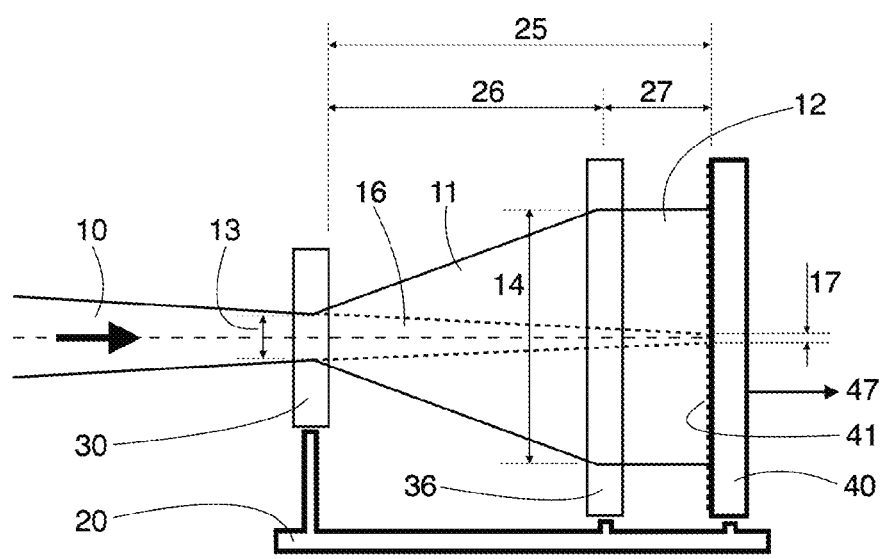
FIG. 2: A schematic representation of a second embodiment of the invention with an expansion device, a collimation device, and a radiation sensor.

A second possible embodiment of the invention schematic is depicted in FIG. 2. This embodiment comprises all elements and characteristics of the first embodiment depicted in FIG. 1. A collimation device 36 is additionally provided, in the second embodiment, positioned between the expansion device 30 and the radiation sensor 40. The collimation device 36 is likewise attached to the support mount 20. The expansion device 30 and the collimation device 36 have a distance 26 from one another. The collimation device 36 and the radiation sensor 40 are positioned at a distance 27 to another. The collimation device 36 reduces the angle range of the laser beam propagated 11. The laser beam 12 propagates further and impinges on the receiving surface 41 of the radiation sensor 40. For the rest, the operating principle of the apparatus corresponds to the first embodiment depicted in FIG. 1.

Figure 3:
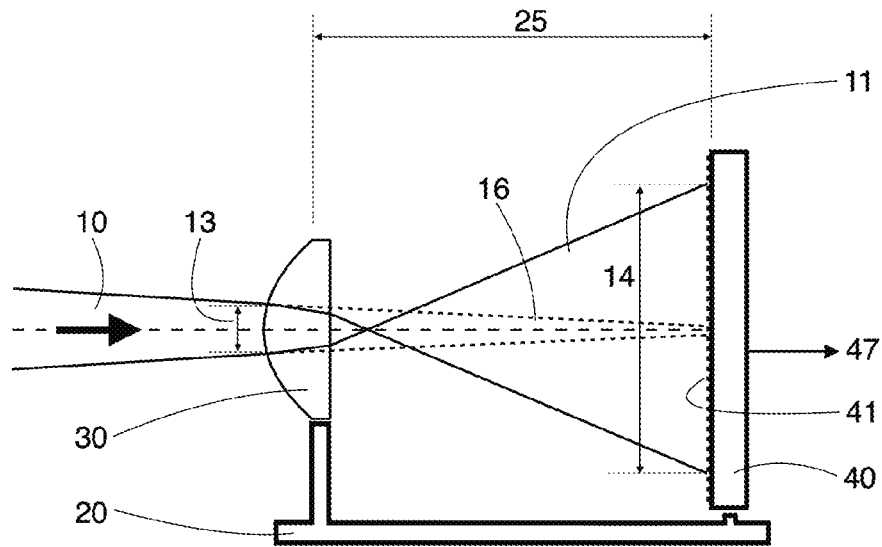
FIG. 3: A schematic representation of one example of implementation of the first embodiment of the invention, in which the expansion device is configured as a converging lens.

FIG. 3 depicts an example of implementation of the first embodiment depicted in FIG. 1. The expansion device 30 is realized, in this example, as a converging lens with a very short focal length. The laser beam 10 is focused by the converging lens and propagates, after the focusing, with a highly expanded cross-section. The laser beam 11 that is propagated impinges, with a large diameter 14, on the receiving surface 41 of the radiation sensor 40.

Figure 4:
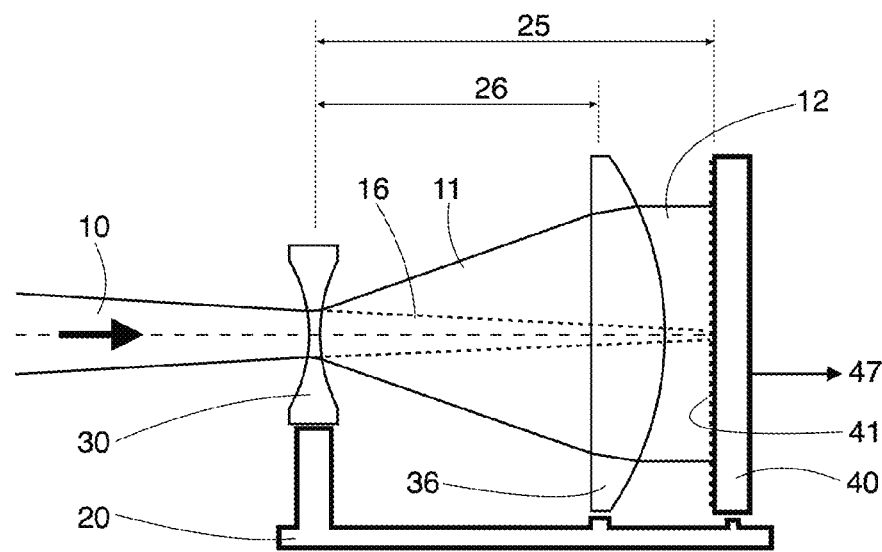
FIG. 4: A schematic representation of one example of implementation of the second embodiment of the invention, in which the expansion device is configured as a diverging lens and the collimation device is configured as a converging lens.

FIG. 4 depicts an example of implementation of the second embodiment depicted in FIG. 2. In this example, the expansion device 30 is implemented as a diverging lens with a very short focal length. The collimation device 36 is implemented as a converging lens.

Figure 5:
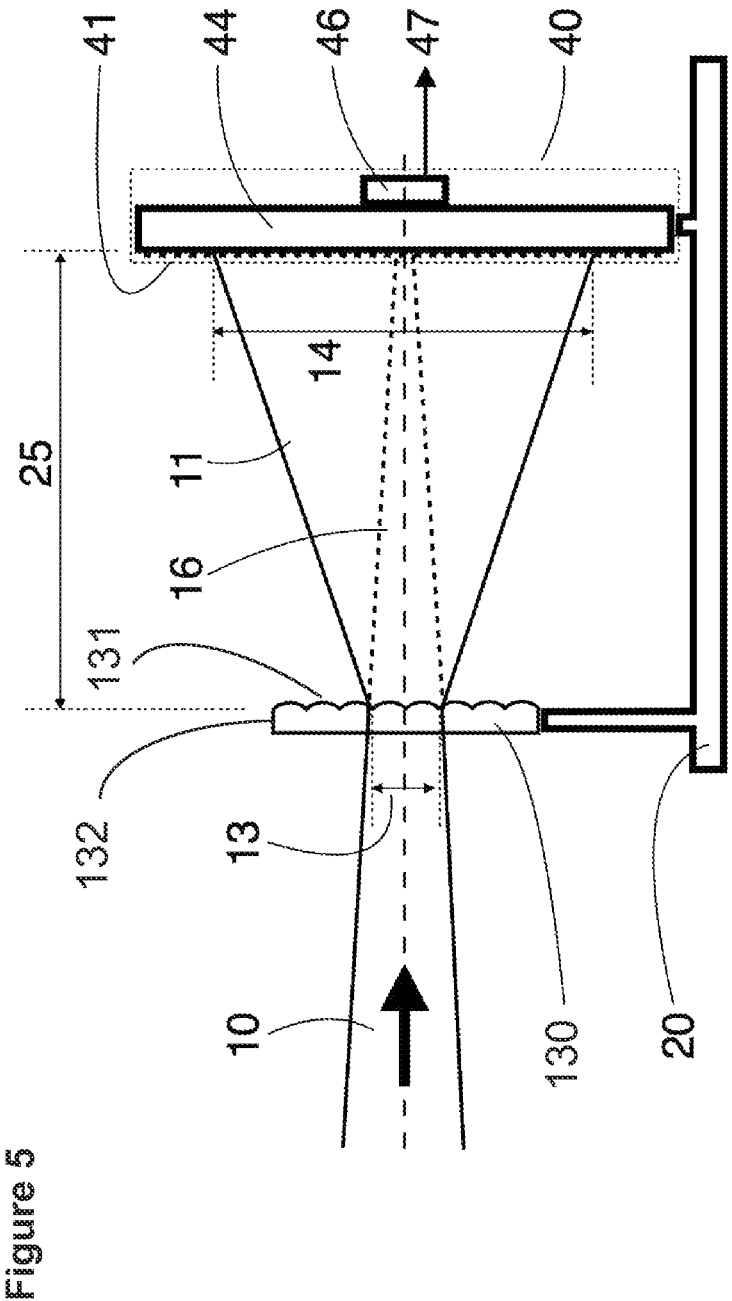
FIG. 5: A representation of an additional example of implementation of the first embodiment of the invention with a lenslet array as an expansion device. The radiation sensor is, by way of example, realized as an absorption body with a temperature sensor.

An additional example of implementation of the first embodiment depicted in FIG. 1 is depicted in FIG. 5. The expansion device 130 is, in this example, configured as a lenslet array which comprises a plurality of lenslets 131 that are all arranged in a common plane 132 that lies transverse to the direction of laser beam 10 or optical axis of same. The individual lenslets of the lenslet array can, as depicted in the diagram, have a convex form. Furthermore, FIG. 5 depicts an example of the construction of the radiation sensor 40. The radiation sensor 40 here contains an absorption body 44 and a temperature sensor 46, which is thermally coupled with the absorption body 44. The receiving surface 41 is a surface of the absorption body 44 and has as high an absorption level as possible. Upon the impinging of the laser beam 10, 11, the beam power is essentially converted into heat, so that the temperature of the absorption body 44 rises. The temperature of the absorption body 44 is measured by the temperature sensor 46. The temperature sensor 46 produces the electrical signal 47.

Figure 6:
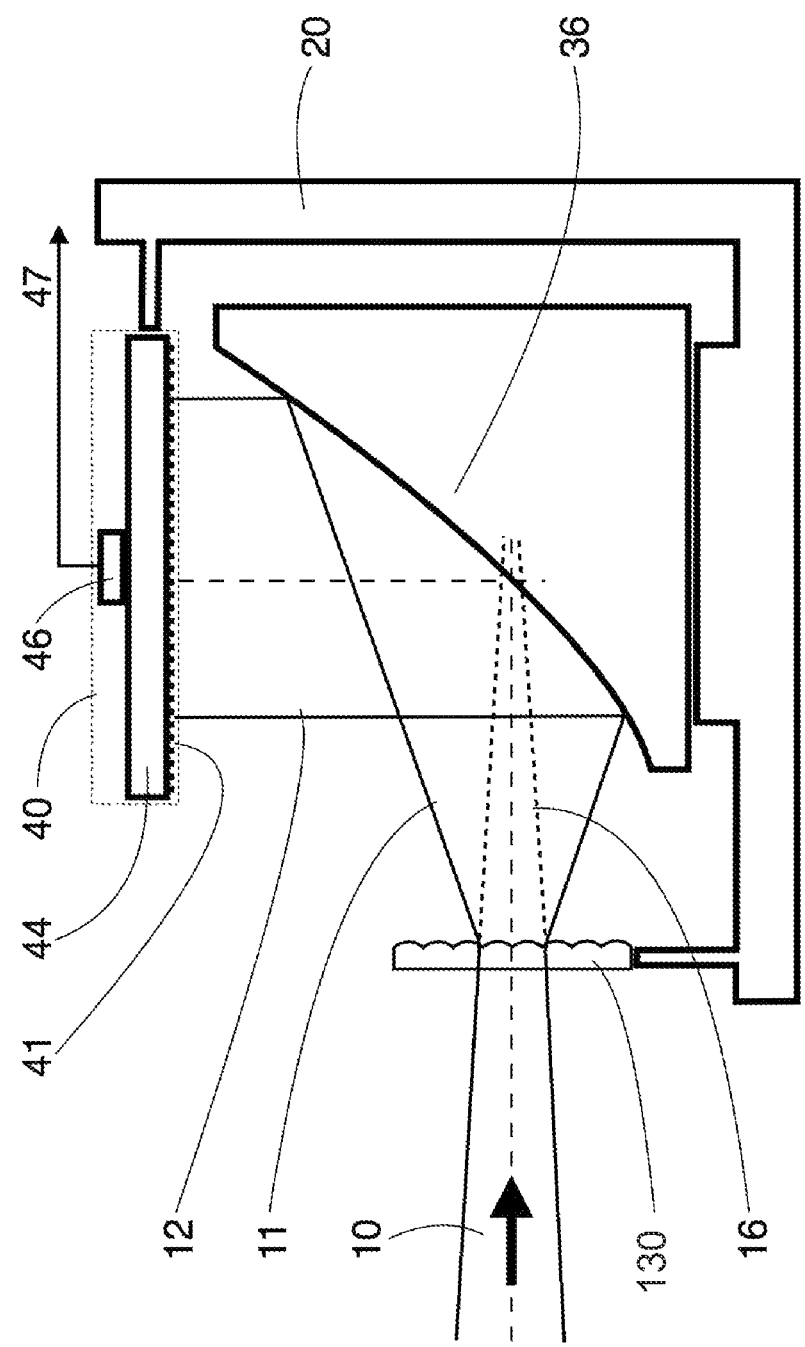
FIG. 6: A representation of an additional example of implementation of the second embodiment of the invention, with a lenslet array as an expansion device and with a concave mirror as a collimation device.

One additional example of implementation of the second embodiment of the invention is depicted in FIG. 6. Similarly to FIG. 5, the expansion device 130 is realized, in this example, as a lenslet array. The second embodiment additionally has a collimation device 36. The collimation device 36 is realized, in this example, as a concave mirror.

Figure 7:
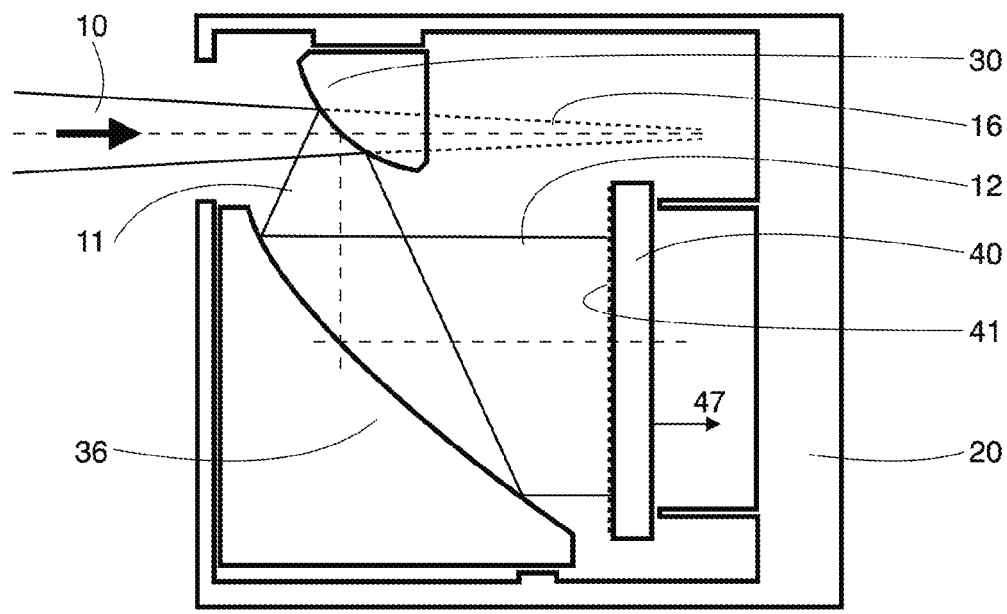
FIG. 7: One further representation of an additional example of implementation of the second embodiment of the invention, with a convex mirror as an expansion device, with a concave mirror as a collimation device, and with a support mount configured as a casing.

FIG. 7 depicts another example of the second embodiment. As in FIG. 6, the collimation device 36 is realized as a concave mirror. The expansion device 30 is, in this example, a convex mirror. The support mount 20 is configured as a casing, which encloses the expansion device 30, the collimation device 36, and the radiation sensor 40. The casing has an opening for the expansion device 30, through which the laser beam 10 can impinge on the expansion device 30.

Figure 8:
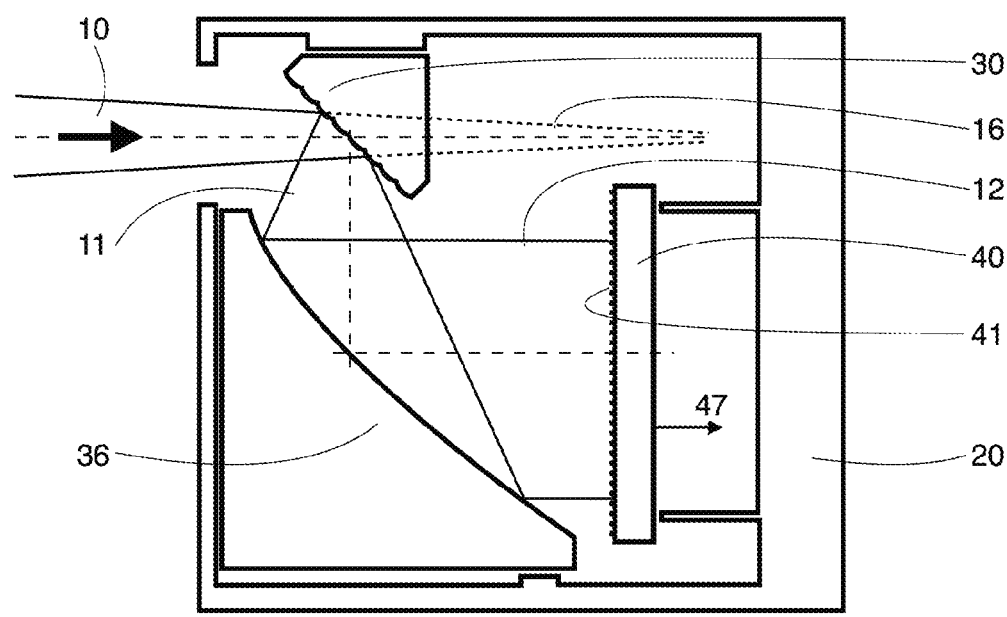
FIG. 8: A representation of one example of implementation of the invention similar to the embodiment depicted in FIG. 7, wherein the expansion device is configured here as a segmented mirror.

Yet another example of the second embodiment is depicted in FIG. 8. This example is similar to the example of an expansion device 30 depicted in FIG. 7, which, in this example, is not a convex mirror, but instead a segmented mirror. The individual facets of the segmented mirror can have a convex form.

Figure 9:
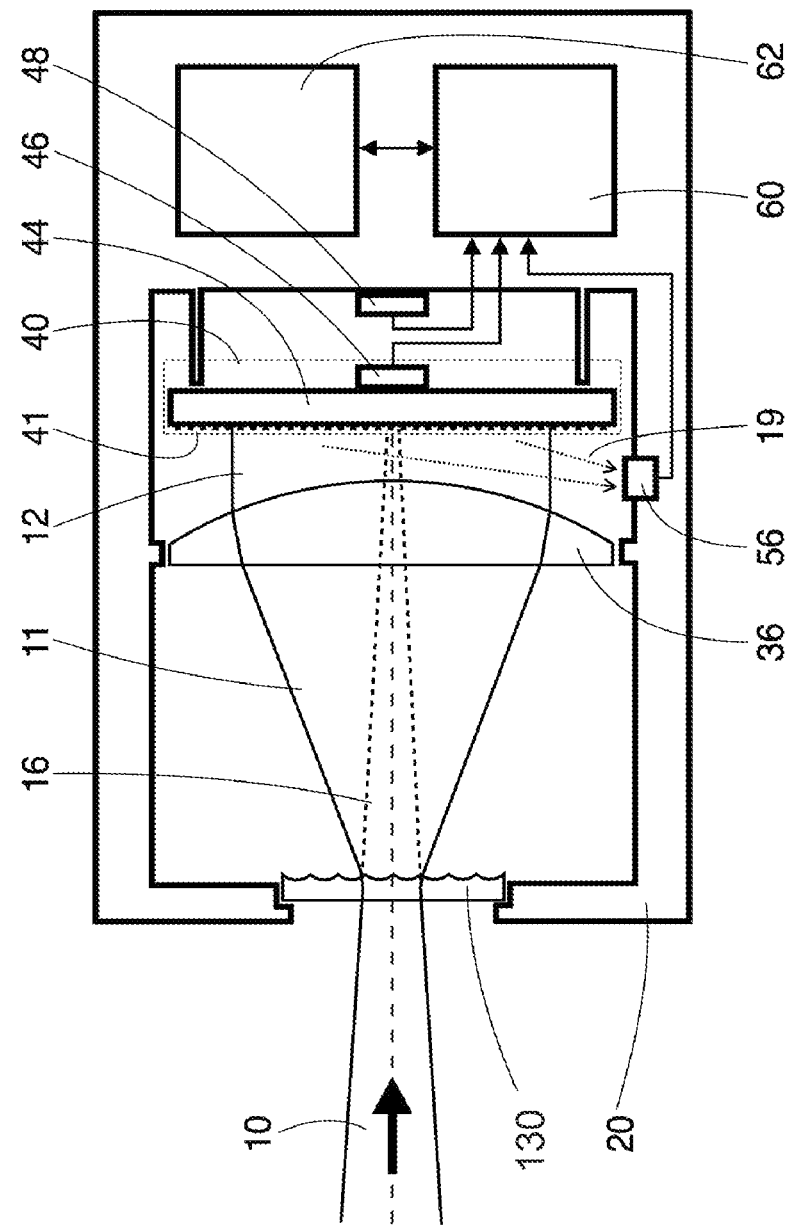
FIG. 9: A representation of one example of implementation of the invention as a compact measuring device, in which the support mount is configured as a casing and an electronic computing unit, as well as an interface, are integrated into the casing.

FIG. 9 schematically depicts an example of implementation of the second embodiment of the invention as an independent measuring device. The expansion device 130 is, in this example, realized as a lenslet array. The individual microlens (lenslets) of the lenslet array can have a concave form, as indicated in FIG. 9. The collimation device 36 is realized as a converging lens. As in the example of implementation of FIG. 5, the radiation sensor 40 contains an absorption body 44 and a temperature sensor 46, which is thermally coupled with the absorption body 44 for the detection of the temperature of the radiation sensor 40. A second temperature sensor 48, which measures a second temperature in the environment of the radiation sensor 40, is provided. For this purpose, the second temperature sensor 48 can be thermally coupled with the casing. Furthermore, a light sensor 56, which records a fraction of the laser beam 10, 11, 12 on the radiation sensor 4, is provided. In the example of implementation depicted, the light sensor 56 is positioned laterally between the collimation device 36 and the radiation sensor 40, so that at least a portion of the receiving surface 41 of the radiation sensor 40 is located in the geometrical-optical detection range of the light sensor 56. The light sensor 56 is consequently able to measure scattered light, which originates from the receiving surface 41 to a slight extent. The signals of the temperature sensor 46, and the second temperature sensors 48, as well as of the light sensor 56, are recorded and processed in an electronic computing unit 60. The data computed by the electronic computing unit 60, such as the power and/or the energy of the laser beam 10, is supplied by means of an interface 62. The support mount 20 is realized here as a casing, which contains the expansion device 30, the collimation device 36, the radiation sensor 40, the second temperature sensor 48, the light sensor 56, the electronic computing unit 60, and the interface 62. The casing has an opening, through which the laser beam 10 can enter toward the expansion device 30.

Figure 10:
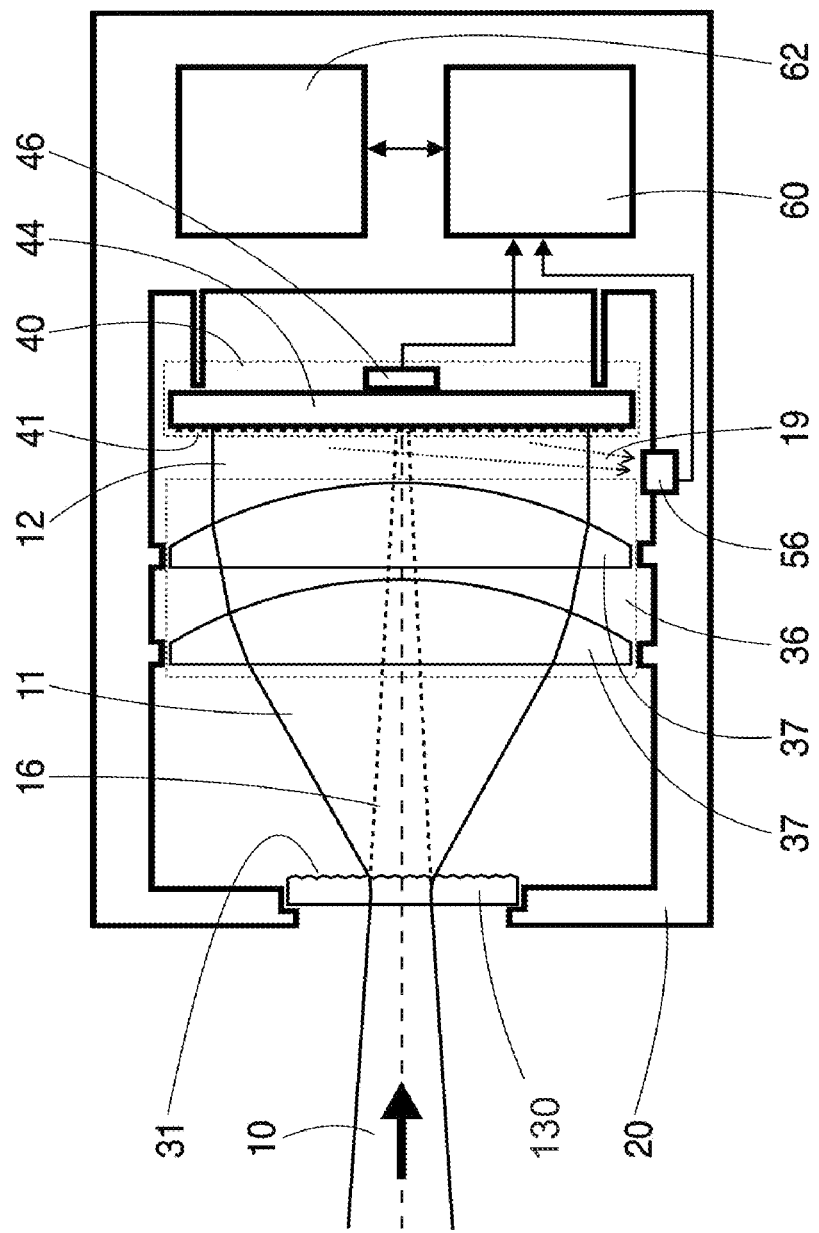
FIG. 10: A representation of an additional example of implementation of the invention as a compact measuring device similar to the embodiment depicted in FIG. 9. The collimation device is realized here as an optics with several convex lenses. The expansion device comprises a light-scattering structure for the increase of the angle range of the radiation.

An additional example of implementation as an independent measuring device is depicted in FIG. 10. In contrast to FIG. 9, for example, the expansion device 30 has, in this example, a light-scattering structure 31 for increasing the angle range of the laser beam 10. The collimation device 36 is realized as an optics consisting of two converging lenses 37.

Figure 11A:
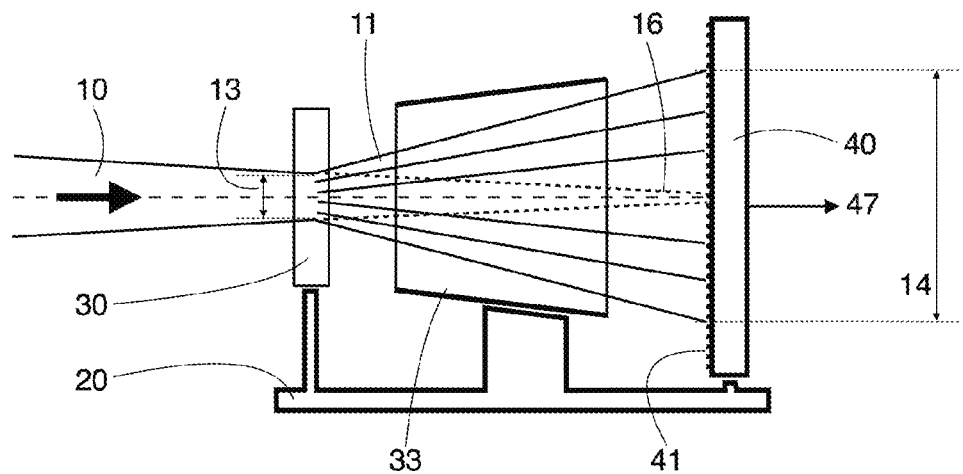
FIG. 11*a*: A schematic representation of a third embodiment of the invention with an expansion device, a beam guiding device, and a radiation sensor.
Figure 11B:
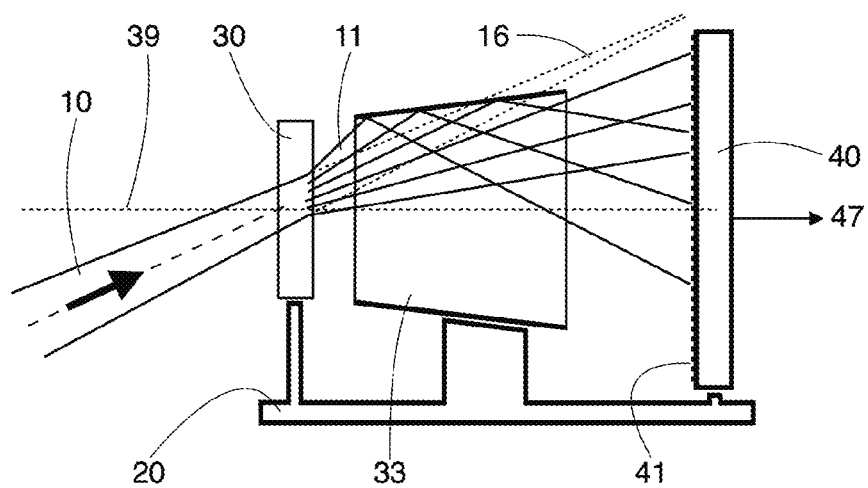
FIG. 11*b*: A representation of a third embodiment of the invention as in FIG. 11*a*, with an obliquely incident laser beam, which is deflected by the beam guiding device onto the central area of the receiving surface of the radiation sensor.

FIGS. 11a and 11b depict a third possible embodiment of the invention in a schematic representation. This embodiment comprises all elements of the first embodiment depicted in FIG. 1. In the third embodiment, a beam guiding device 33, which is positioned between the expansion device 30 and the radiation sensor 40, is additionally provided. The beam guiding device 33 can, for example, be a prism, on the lateral surfaces of which portions of the propagating laser beam 11 can be deflected through total reflection. In the example of implementation depicted, the beam guiding device 33 is so dimensioned that the beam guiding device 33 is without effect if the laser beam 10 is axially aligned, as depicted in FIG. 11a, If the laser beam is obliquely irradiated, i.e., if the laser beam 10 has an angle to the optical axis 39 of the device, as depicted in FIG. 11b, then a portion of the propagating laser beam 11 is deflected into the direction of the receiving surface 41 of the radiation sensor 40. The laser beam 11 on the receiving surface 41 is consequently centered by means of the beam guiding device 33. For the rest, the operating principle of the apparatus corresponds to the first embodiment depicted in FIG. 1.

Figure 12:
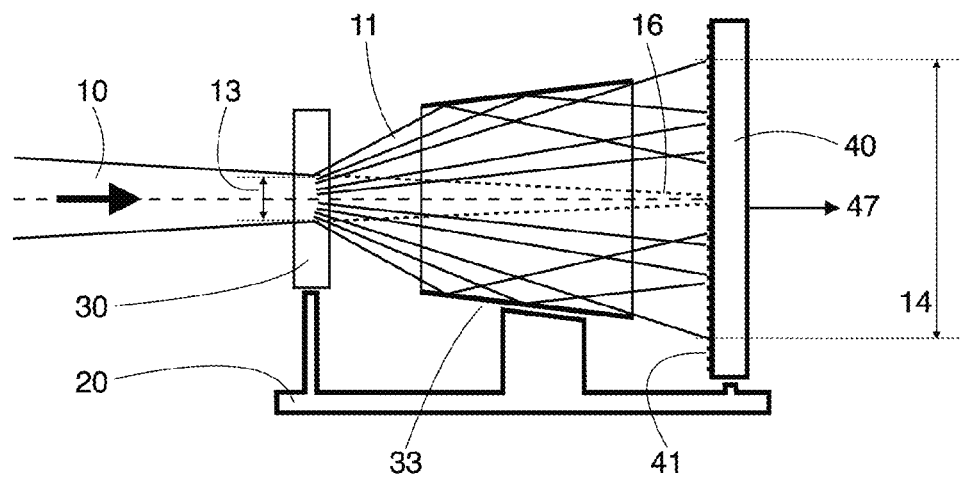
FIG. 12: A representation of an additional example of implementation of the third embodiment of the invention, in which the beam guiding device, by the deflection of partial areas of the propagating laser beam, reduces the angle range of the radiation.

A further example of the third embodiment is schematically depicted in FIG. 12. In this example of implementation, the beam guiding device 33 is so dimensioned that lateral areas of the propagating laser beam 11 are deflected at large angles to the beam axis through reflection onto the lateral surfaces of the beam guiding device 33.

Figure 13:
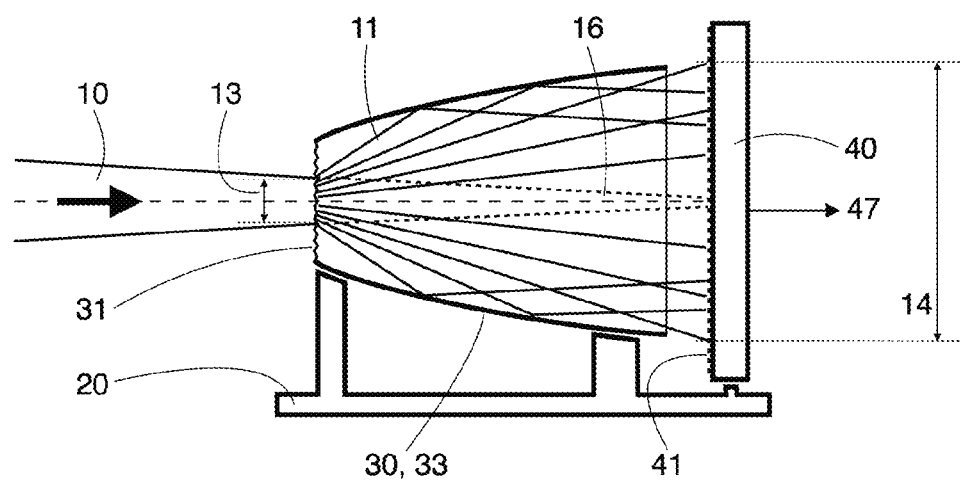
FIG. 13: A schematic representation of a fourth embodiment of the invention, in which the expansion device is simultaneously configured as a beam guiding device and as a collimation device.

FIG. 13 depicts a fourth possible embodiment of the invention in a schematic representation. In this embodiment, the expansion device 30 integrates several functions into one component. In the example depicted, the expansion device 30 has a light-scattering structure 31 on the front surface or on the beam entry surface of the expansion device 30. The light-scattering structure 31 brings about an increase in the angle range of the laser beam 10. The lateral surfaces of the expansion device 30 have an inclination and/or a curvature, so that the radiation components of the propagating laser beam 11 reflected onto the lateral surfaces are deflected to the receiving surface 41 of the radiation sensor 40 and the angle of the deflected radiation components to the beam axis is reduced. The expansion device 30 in this embodiment consequently simultaneously fulfills the function of a beam guiding device and, at least partially, of a collimation device. For the rest, the operating principle of the apparatus corresponds to the first embodiment depicted in FIG. 1.

Figure 14:
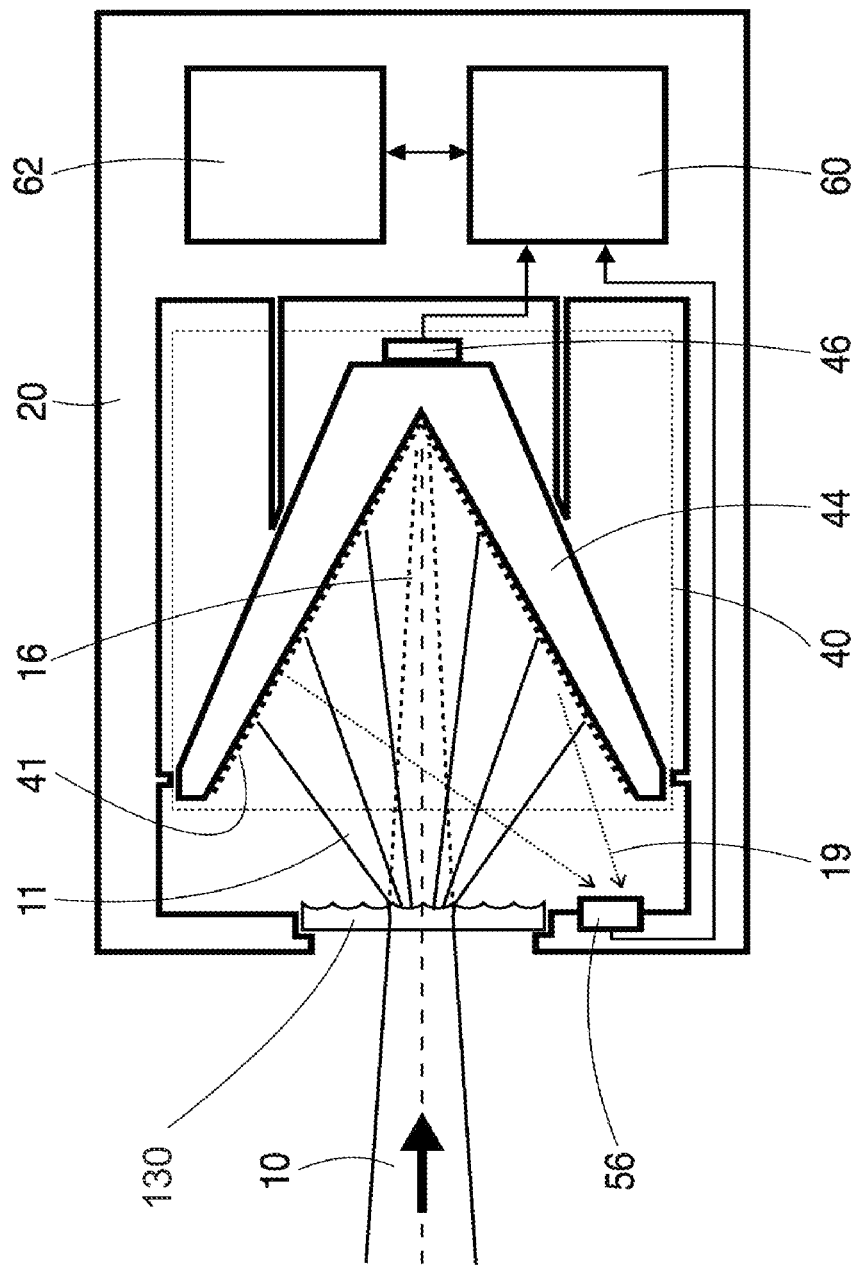
FIG. 14: A representation of an additional example of implementation of the first embodiment of the invention, in which the radiation sensor comprises an absorption body in the form of a hollow body with a conical receiving surface.
Figure 15:
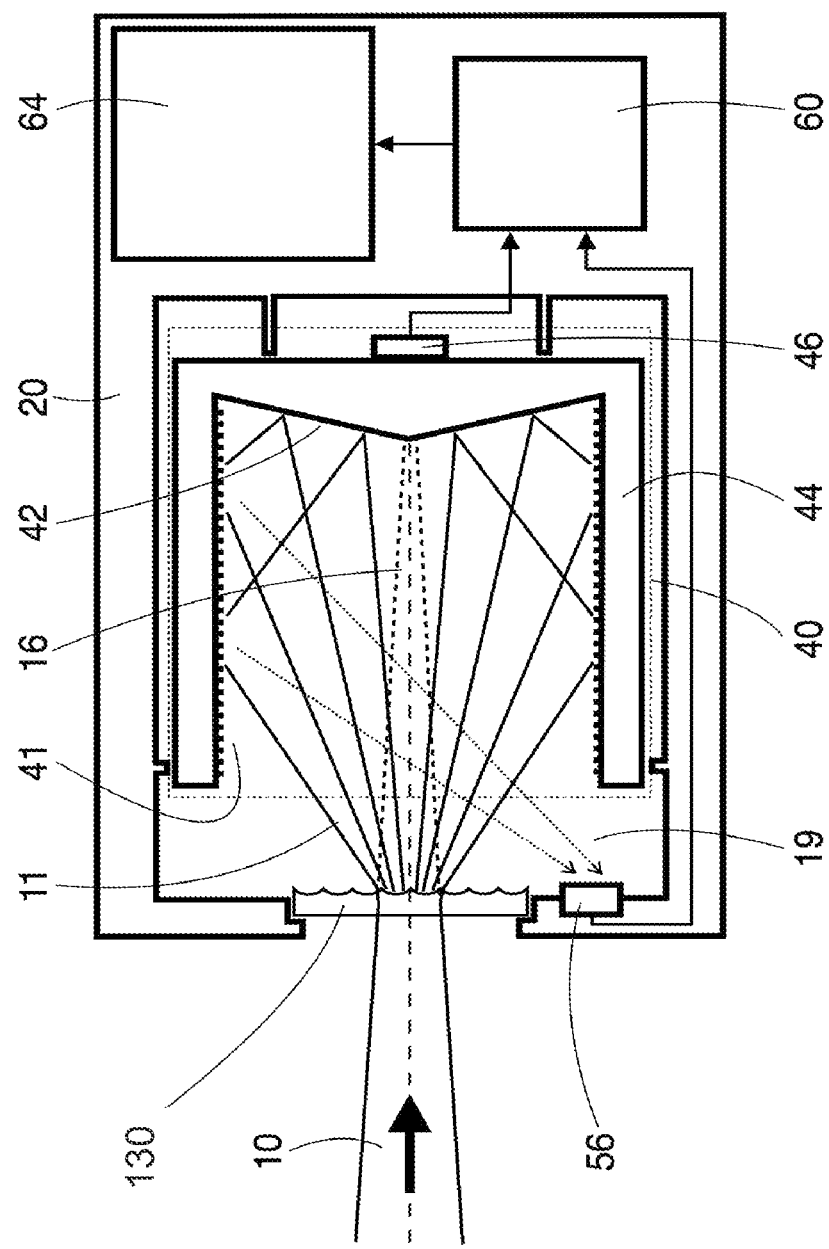
FIG. 15: A representation of another example of implementation of the first embodiment of the invention, in which the radiation sensor contains an absorption body in the form of a hollow cylinder and a portion of the receiving surface is configured in a reflecting manner.

An additional example of implementation of the first embodiment is schematically depicted in FIG. 14. In this example, the radiation sensor 40 contains an absorption body 44 and a temperature sensor 46, which is thermally coupled with the absorption body 44. The absorption body 44 is designed as a hollow space absorber, in this example, as a hollow cone or an inner cone, wherein the receiving surface 41 is increased and the cross-section of the laser beam propagated 11 is distributed onto a larger surface. Furthermore, a light sensor 56 is provided, which receives a portion of the laser beam 11 partially scattered at the receiving surface 41. The signals of the temperature sensor 46 and the light sensor 56 are recorded and processed in the electronic computing unit. An interface 62 is provided for the exchange of data with an external display unit or an external device. FIG. 15 depicts yet another example of implementation of the first embodiment. Similarly to FIG. 14, the absorption body 44 is designed as a hollow space absorber, in this example, as a hollow cylinder. A partial area 42 of the receiving surface 41, here the base surface of the hollow cylinder, is configured to be reflecting or partially reflecting. By that means, the radiation impinging on this area is guided to the cylindrical lateral surfaces. The base surface of the hollow cylinder is provided, for this purpose, with a flat cone shape. Instead of an interface, a display device 64, by means of which the data determined by the electronic computing unit 60 can be displayed, is provided in this example.

Figure 16:
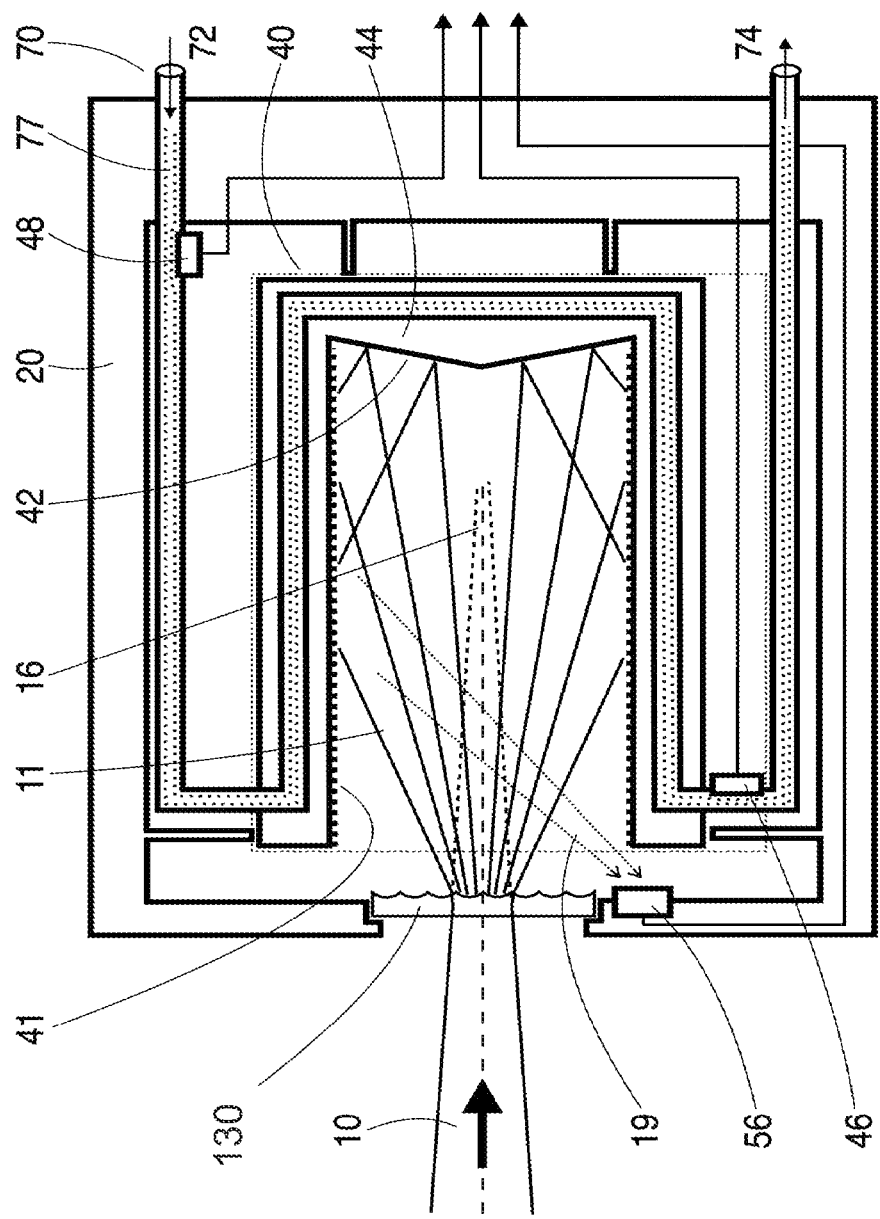
FIG. 16: One further representation of an additional example of the first embodiment of the invention, in which the radiation sensor contains an absorption body in the form of a hollow cylinder and in which radiation sensor is equipped with a cooling device.

An example of implementation of the first embodiment, which is also suitable for the continuous measurement of the power of the laser beam 10, is depicted in FIG. 16. The radiation sensor 40 is, by way of example, constructed similarly to the example depicted in FIG. 15. A cooling device 70 is provided for the removal of the heat absorbed by the absorption body 44. A coolant 77 is brought into the cooling device 70 through a coolant inlet 72, flows through the absorption body 44 of the radiation sensor 40, and is drained through a coolant outlet 74. The coolant 77 is guided through pipes, boreholes or channels inside the absorption body 44 and absorbs the heat of the absorption body 44. The temperature sensor 46 coupled with the absorption body 44 is positioned downstream in relation to the coolant throughflow direction, where the heated coolant leaves the absorption body 44 and thus records the temperature of the heated coolant. The second temperature sensor 48 is positioned upstream, before the coolant is guided into the absorption body 44, and thus records the inlet temperature of the coolant 77. The throughflow quantity of the coolant 77 can be determined by means of a throughflow sensor, which is not depicted. The power of the laser beam 10 is determined from the difference between the temperatures measured by the temperature sensors 46 and 48 and the throughflow quantity.

FIG. 17 depicts an example of implementation for the continuous measurement of the second embodiment. The cooling device 70 corresponds to the example depicted in FIG. 16. Instead of a hollow space absorber, as in FIG. 16, a simple flat absorption body 44 is provided here. The absorption body 44 thereby has a minor thermal mass, through which the response time of the temperature change, and thus of the signal of the temperature sensor 46, is reduced. The temperature sensor 46 of the radiation sensor 40 is positioned downstream at the coolant outlet of the absorption body 44, and the second temperature sensor 48 is positioned upstream and in front of the absorption body. For the optimal absorption of the radiation on the receiving surface 41, a collimation device 36 is provided in front of the radiation sensor 40, by means of which the angle range of the laser beam propagated 11 is reduced. The collimation device 36 is, in this example, a converging lens which collimates the propagating laser beam 11, so that the further propagating laser beam 12 impinges essentially perpendicularly to the receiving surface 41. Prior to this, the angle range of the laser beam 10 is increased by means of the expansion device 30 for the expansion of the laser beam 10. The signals of the temperature sensors 46 and 48 are recorded and processed by the electronic computing unit 60. The data computed are transmitted to an external device by means of an interface 62.

DETAILED DESCRIPTION OF THE INVENTION

A solution for the problem stated is given by providing a simple method and a compact apparatus for the direct and precise measurement of the power and/or energy of a laser beam, which makes a measurement possible even in regions close to the beam focus.

For the solution of the task stated, there is proposed an apparatus which contains a support mount 20, an expansion device 30 and a radiation sensor 40 with a receiving surface 41. The expansion device 30 and the radiation sensor 40 are positioned, by means of the support mount 20, at a distance 25 from one another. The apparatus is adapted for collecting a laser beam 10. The laser beam 10 first of all impinges on the expansion device 30. The laser beam 10 has a diameter 13 in the region of the expansion device 30. The expansion device 30 increases the angle range of the laser beam 10. The term angle range here means the range of distribution of the angles of all partial beams of the laser beam to the beam axis. After the increase of the angle range by the expansion device 30, the laser beam 10 propagates between the expansion device 30 and the radiation sensor 40, indicated in this region with the reference number 11, with an expanded beam cross-section. The laser beam 11 propagated impinges on the receiving surface 41 of the radiation sensor 40. The laser beam 11 has a diameter 14 on the receiving surface 41.

The diameter 14 on the receiving surface 41 is greater than the diameter 13 of the laser beam 10 in the region of the expansion device 30. The receiving surface 41 of the radiation sensor 40 encloses at least 90% of the cross-section surface of the laser beam propagated 11. Regarding a circular beam cross-section of the laser beam propagated 10, 11, the diameter of the receiving surface 41 is accordingly greater than or at least equal to 0.95 times the diameter 14 of the laser beam 11. Furthermore, the laser beam 11 propagated is accordingly centered on the receiving surface 41 in such a way that a maximum of 10% of the cross-section surface of the laser beam 11 is located outside the receiving surface 41. The radiation sensor 40 generates an electrical signal 47, which is dependent on the power or energy of the laser beam 10, 11. The power or energy value of the laser beam 10, 11 is determined from the electrical signal 47.

The laser beam 10 can be focused and the apparatus in accordance with the invention can be positioned in the region of the focus of the laser beam 10. The laser beam 10 can have a very small diameter 17 in the area of the focus, if the laser beam 10 spreads unhindered, that means without an expansion device. The virtual propagation of the laser beam 10 without an expansion device 30 is indicated, for example, in FIG. 1 as dotted lines with the reference number 16. The diameter 17 in the focus area can amount to the order of magnitude of 0.1 mm, for example, and the power of the laser beam 10 can amount to 1 kW, for example. The power density then is in an order of magnitude of approximately 10 MW/cm$^2$. Virtually all non-transparent materials are immediately melted or perforated at such power densities. No detector of any type can resist such power densities. Thus, the expansion device 30 is positioned at the distance 25 in front of the radiation sensor 40. The expansion device 30 increases the angle range of the laser beam 10—that is to say, the width of the distribution of the angle of all partial beams of the laser beam 11 to the beam axis is greater after passing the expansion device 30. A collimated beam, for example, has an angle range of almost zero or far below 1°. A laser beam focused by means of a processing optics typically has an angle range of a few degrees. The expansion device 30, for example, can be configured in such a way as to increase the angle range by ±5°, and therefore over a width of the distribution of 10°, and the distance 25 between the expansion device 30 and the radiation sensor 40 can amount to 50 mm, for example. The beam diameter 14 on the receiving surface is then barely 9 mm large, and the power density at 1 kW amounts to less than 2 kW/cm$^2$. In comparison with the above example of the beam in the focus area without an increase in the angle range, the power density is accordingly reduced by almost 4 orders of magnitude. The reduced power density can be processed by many detectors without damage, at least in the short-term.

It is provided, in a possible embodiment, that the distance 25 between the expansion device 30 and the radiation sensor 40 is in the range of 10 mm to 200 mm. The distance 25 can, in particular, amount to 20 mm to 100 mm.

The increase of the angle range by means of the expansion device 30 can be within a range of ±1° to ±50°. The increase in the angle range can, in particular, be in the range of ±2° to ±30°.

The expansion device 30 can be configured in various ways. The increase of the angle range can be carried out through refraction, reflection, diffraction, or scattering. It is not necessary for an intensity distribution, a beam profile, or a beam parameter product of the laser beam 10 to be maintained, but only the total power or total energy integrated over the cross-section of the beam must essentially be maintained. It is common to all embodiments of the expansion device 30 that the laser beam 10 passes the expansion device 30 almost without attenuation. The absorption level of the expansion device 30 is below one percent. If the expansion device 30 is a transmitting optical component, then the transmission level is greater than 90%, preferably greater than 99%. For this purpose, the beam entrance and exit surfaces of the expansion device 30 can be provided with an antireflection coating. If the expansion device 30 is a reflecting optical component, then the degree of reflection is greater than 99%.

The expansion device 30 can be an optical lens, for example. The focal length of the optical lens is a fraction of the distance 25 between the expansion device 30 and the radiation sensor 40. It is provided that the amount of the focal length of the optical lens amounts to a maximum of ⅓ of the distance 25. The optical lens can be a concave lens or a convex lens—that is to say, a diverging lens or a converging lens. The advantage of a diverging lens consists of the fact that, upon the same amount of focal length of the lens, the distance 25 can be selected to be somewhat shorter, in order to achieve an equally increased beam diameter 14 on the receiving surface 41. FIG. 3 depicts an example for an embodiment of the expansion device 30 as a converging lens, while a diverging lens is depicted as an expansion device 30 in FIG. 4.

The expansion device 130 can also be an array of microlens (lenslets) or a lenslet array, i.e., the expansion device 130 comprises, in this embodiment, several individual microlens (lenslets) that are positioned next to one another or side by side along or in a common plane transverse to the direction or optical axis of the laser beam 10. The special feature in the use of a lenslet array as an expansion device 130 consists of the fact that an increase of the angle range can thereby be achieved, the width of the angle distribution being not dependent on the diameter 13 of the laser beam 10 in the area of the expansion device 130, if the lateral dimensions of the individual microlens of the lenslet array are chosen to be small enough. In order to achieve this, the lateral dimension or the width of the microlenses are chosen to be smaller than or a maximum of equal to the diameter 13 of the laser beam 10 in the area of the expansion device 130. The width of the individual microlens can be in the range of 0.1 mm to 5 mm, for example. The amount of the focal length of the individual microlens can be in the range of 0.3 mm to 20 mm. The ratio of the amount of the focal length of the individual microlens to the width of the individual microlens can be in the range of 2 to 30, for example. The individual microlens of the lenslet array can have a positive or a negative refractive power that is to say, the surfaces of the individual microlens can be curved convexly or concavely. Examples of implementation for a convex lenslet array are depicted in FIGS. 5 and 6, while the expansion device 30 is realized in FIGS. 9 and 14 to 17 as a concave lenslet array.

The expansion device 30 can also have a light-scattering structure 31. The light-scattering structure 31 spreads the radiation of the laser beam 10 in the forward direction and in a limited angle range. The light-scattering structure 31 can be realized as a boundary surface of an optical transparent material with a level of roughness or waviness, for example. The radiation is deflected on the irregularities of the rough or wavy boundary surface by refraction at various angles. The light-scattering structure 31 can also be a structure with locally varying refractive index, for example.

The increase of the angle range by the expansion device 30 can also be achieved by means of diffraction. For this purpose, the expansion device 30 can have a light-diffracting structure. The light-diffracting structure can be applied to a boundary surface of the expansion device 30 by means of a lithographic process, for example.

The expansion device 30 can also be a diffusor. Optical elements that divert the impinging radiation into various statistically distributed angles are generally termed diffusors. This can be achieved, as already explained, by means of a light-scattering structure 31 or by means of a light-diffracting structure, for example.

The expansion device 30 can also be a curved mirror or concave mirror or a convex mirror. The difference to the use of an optical lens consists of the fact that the beam path is folded. It is provided that the absolute value of the radius of curvature of the concave or convex mirrors amounts to a maximum of ⅔ of the distance 25 between the expansion device 30 and the radiation sensor 40. An example of implementation for a convex mirror as an expansion device 30 is depicted in FIG. 7.

The expansion device 30 can also be a segmented mirror. In a segmented mirror, several individual facets are positioned next to one another. The individual facets of the segmented mirror can be curved convexly or concavely. Similar to an lenslet array 130, an increase of the angle range can be achieved with a segmented mirror as an expansion device 30, the width of the angle distribution being not dependent on the diameter 13 of the laser beam 10 in the area of the expansion device 30, if the lateral dimensions of the individual facets of the segmented mirror are chosen small enough. FIG. 8 depicts an example of implementation in which a segmented mirror is used as an expansion device 30.

Various detectors can be used as a radiation sensor 40. The radiation sensor 40 has a receiving surface 41. The receiving surface 41 is sufficiently large that the entire beam cross-section of the laser beam 10, 11, 12, or at least 90% of the cross-section surface of the laser beam of the receiving surface 41, is measured. Within the cross-section of the laser beam, the intensity of the radiation is usually dependent on location. Many laser beams have an approximately Gaussian intensity distribution. The intensity distribution in the propagating laser beam 11 can be changed by the expansion device 30. The radiation sensor 40 measures the entire, or at least almost the entire, cross-section of the beam, and thus produces a signal value that corresponds to the integral value of the intensity distribution. The integral value of the intensity distribution is the intensity of the laser beam 10, 11, 12 integrated over the receiving surface. The signal value is consequently dependent on the total power or total energy of the laser beam. The signal value is emitted as an electrical signal 47.

The radiation sensor 40, for example, can be a large-area photodiode or a large-area semiconductor sensor. The radiation sensor 40 can also be a pyroelectrical detector or a pyrometer. The radiation sensor 40 can also be a so-called thermopile, i.e., a thermal column or a thermal chain coupled with an absorption layer.

The radiation sensor 40 can also be configured as a calorimetrical sensor. For this purpose, the radiation sensor 40 comprises an absorption body 44 and a temperature sensor 46. The temperature sensor 46 is thermally coupled with the absorption body 44 in order to measure the temperature of the absorption body 44. The receiving surface 41 here is a surface of the absorption body 44. The receiving surface 41 has a high absorptance. For this purpose, the receiving surface can be coated black or absorbtive. The receiving surface 41 can also have a structuring, such as a grooved pattern, for example. The laser beam 10, 11, 12 impinging on the receiving surface 41 is absorbed for the most part and converted into heat. The temperature of the absorption body 44 is thereby increased, which fact is recorded by the temperature sensor 46. The temperature sensor 46 generates the electrical signal 47. The radiation sensor 40 or the absorption body 44 is attached to the support mount 20 or to the support mount 20, which is configured as a casing, in a thermally insulated manner. For this purpose, the support mount elements, which are connected with the radiation sensor 40 or the absorption body 44 are manufactured from a thermally lowly conductive material, for example. By means of the thermally insulated attachment, uncontrolled heat flows from the absorption body 44 into the environment, which can reduce the precision of the measurement, are reduced. In many detectors, the level of the generated signals is dependent, to a minor degree, on the position of the beam on the detector and on the impingement angle of the beam on the detector. In order to achieve a high precision in the measurement, care must be taken that the beam impinges, to the greatest extent possible, on the detector axially symmetrically or centrally, and that the angle of incidence diverges as little as possible from the perpendicular incidence.

For the additional improvement of the measuring accuracy, a collimation device 36 therefore is, in an additional possible embodiment of the invention, positioned between the expansion device 30 and the radiation sensor 40, as schematically depicted in FIG. 2. The collimation device 36 is positioned at a distance 26 from the expansion device 30. The collimation device 36 reduces the angle range of the propagating laser beam 11, which was increased by the expansion device 30 prior to this. It is thereby achieved that the angles of all partial beams of the laser beam to the beam axis are as small as possible after passing the collimation device 36. The laser beam propagating after the collimation device 36, which is indicated in FIG. 2 in this area with the reference number 12, therefore approximately retains its cross-section or diameter—that is to say, the diameter of the laser beam 11 in the area of the collimation device 36 is approximately equal to the diameter 14 of the laser beam 11, 12 on the receiving surface 41. The partial beams of the laser beam 12 propagating after the collimation device 36 therefore impinge approximately perpendicularly on the receiving surface 41 of the radiation sensor 40.

The collimation device 36 can be a converging lens or a convex lens, a Fresnel lens, a gradient index lens, an optics consisting of several lenses, or a concave mirror, for example. The collimation device has a positive focal length $f_K$. In one possible embodiment of the invention, the focal length of the collimation device 36 can be greater than or equal to the distance 26 between the expansion device 30 and the collimation device 36, so that:

$$f_K \geq d_{AK}$$

$f_K$ here is the focal length of the collimation device 36, and $d_{AK}$ is the distance 26 between the expansion device 30 and the collimation device 36. It should here be taken into account that the distance $d_{AK}$ 26 is defined by distance from the expansion device 30 to the principal plane (or principal surface) of the collimation device 36.

Furthermore, the focal length $f_K$ of the collimation device 36 can be smaller than or equal to the following value:

$$f_K \leq d_{AK} \varnothing_{SE}/(\varnothing_{SE} - \varnothing_{SA})$$

$\varnothing_{SA}$ here is the diameter 13 of the laser beam 10 in the area of the expansion device 30, and $\varnothing_{SE}$, is the diameter of the laser beam 11, 12 on the receiving surface 41 or in the area of the collimation device 36.

FIGS. 4 and 9 depict examples with a converging lens as the collimation device 36. In FIG. 10, an optics consisting of two convex lenses 37 is depicted as a collimation device 36. FIGS. 6, 7 and 8 depict an example of a concave mirror as a collimation device 36.

In one additional possible embodiment of the invention, a beam guiding device 33, which is positioned between the expansion device 30 and the radiation sensor 40, is provided. By means of the beam guiding device 33, the impingement position of the beam spot on the receiving surface 41 can be optimized through the fact that the beam guiding device 33 holds the laser beam 11 inside a desired cross-section.

The beam guiding device 33, for example, can be configured as a light-conducting prism, and thus as a prism made from a transparent material. The prism has a beam entry surface, a beam exit surface, and lateral surfaces. On the lateral surfaces of the prism, partial beams of the laser beam 11, which have a very great angle to the axis, are reflected and thus deflected in the direction of the central area of the radiation sensor 40. The reflection on the lateral surfaces of the prism can take place through total internal reflection. The lateral surfaces of the prism can also be supplied with a reflective coating. The beam guiding device 33 can also be a kaleidoscopic arrangement of mirrors. FIGS. 11a, 11b and 12 depict example of implementation of the invention with a beam guiding device 33. The form of the beam guiding device 33 can, for example, be a cylindrical or conical rod, or a rod with a triangular, square, pentagonal, hexagonal, or octagonal cross-section surface. The lateral surfaces can be inclined to the axis—that is to say, the cross-section of the beam exit surface can be greater than the cross-section of the beam entry surface. Through the inclination of the lateral surfaces, the angle to the axis of the partial beams of the laser beam 11, which is reflected onto the lateral surfaces, is reduced. The beam guiding device 33 can thereby bring about a reduction of the angle range of the laser beam 11, similar to the collimation device 36. The reduction of the angle range by the beam guiding device can be optimized by making the lateral surfaces inclined and, in addition, have a curvature, as is depicted in FIG. 13 by way of example.

Yet another additional embodiment of the invention is depicted in FIG. 13, in which the expansion device 30 and the beam guiding device 33 are integrated into one component. For that purpose, the entry surface of the beam guiding device 33 can be configured as an expansion device 30. The entry surface can, for example, be curved concavely, have a surface with lens facets arranged as an array, or have a light-scattering structure 31.

The invention has numerous advantages compared to the state of the art:
- The invention makes possible the direct measurement of the power or the energy of a laser beam without beam attenuation, and high precision can be achieved by that means.
- The power and/or energy density of the radiation on the radiation sensor is significantly reduced.
- The invention makes possible measurements in the focus region of a focused laser beam and thereby has a significantly greater field of application than conventional measuring devices, because conventional measuring devices must be positioned well outside the focus region in order to avoid damage to the detector.
- The impingement angle of the radiation on the receiving surface of the radiation sensor can be kept approximately constant independently of the entrance angle of the laser beam and close to the perpendicular incidence, through which precise and reproducible measurements, in particular, are made possible,
- The impingement position of the beam cross-section on the receiving surface of the radiation sensor can be held, independently of the entrance angle and the entrance position of the laser beam, within a narrow range and close to the center of the radiation sensor, through which the precision and reproducibility of the measurements can be further increased.
- The apparatus in accordance with the invention can be constructed very compactly.

The invention can be further developed, corresponding to the embodiments listed in the following and the additionally listed characteristics, in the most varied manner and advantageously, without leaving the scope and the task of the invention. Additional embodiments of the invention are provided by different combinations of the described characteristics, even if not every possible embodiment is described or depicted in the figures.

With an implementation of the radiation sensor 40 as a calorimetrical sensor, the absorption body 44 can be configured in the most varied ways. The absorption body can be a hollow space absorber, for example. The hollow space can be formed in different ways. The absorption body 44 can be configured conically or tapered, as depicted in FIG. 14. The absorption body 44 can also have a concavely curved receiving surface.

The absorption body 44 can also be a hollow cylinder opened on one side, as depicted in FIGS. 15 and 16. It can be provided to mainly absorb the radiation on the cylindrical inner surfaces of a hollow cylinder. For this purpose, a partial area 42 of the receiving surface 41 can be configured to be reflecting. The reflecting partial area 42 can be in the area of the base surface or the ground surface of the hollow cylinder. The area of the base surface or ground surface of the hollow cylinder can have the form of a flat cone in order to reflect the radiation impinging there to the cylindrical inner surface.

The radiation sensor 40 realized as a calorimetrical sensor can also be equipped with a cooling device 70. In the cooling device 70, a coolant 77 is fed through a coolant inlet 72 and drained through a coolant outlet 74. Between the coolant inlet 72 and the coolant outlet 74, the coolant 77 is guided through a system of pipes, boreholes, channels or other hollow cavities, which are in at least partially thermal contact with the absorption body 44 or which lead through the absorption body 44. The coolant 77 consequently absorbs the heat of the absorption body 44 and dissipates it. The temperature sensor 46 is positioned at a point on which the coolant 77 is conveyed out of the absorption body 44, and consequently records the temperature of the heated coolant.

The invention can, furthermore, contain a second temperature sensor 48. The second temperature sensor 48 is positioned in the vicinity of the radiation sensor 40 and is not thermally coupled with the absorption body 44. The second temperature sensor 48 consequently measures a second temperature in the vicinity of the radiation sensor 40 or the absorption body 44. For this purpose, the second temperature sensor 48 can be attached to the support mount 20 or to or in the support mount 20 realized as a casing, as depicted in FIG. 9. By the detection of the second temperature, the temperature increase of the absorption body 44, from which the power or the energy of the laser beam is computed, can be determined precisely. In addition, by the detection of the second temperature, the magnitude of the uncontrolled heat flows of the absorption body 44 into the environment can be estimated, and the precision of the computation of the power or the energy of the laser beam can thereby be improved.

If the radiation sensor 40 is equipped with a cooling device 70, then the second temperature sensor 48 can be positioned at the point of the coolant feed, before the coolant is guided into the absorption body 44. The second temperature sensor 48 consequently measures the base temperature or the inlet temperature of the coolant 77. The dissipated heat, and thereby the power of the laser beam 10, 11, 12, can consequently be determined from the temperature difference between the temperature sensor 46 and the second temperature sensor 48. FIGS. 16 and 17 depict corresponding examples of implementation.

The apparatus in accordance with the invention can moreover be equipped with a light sensor 56. The light sensor 56 is configured for the detection of a slight radiation component formed by the laser beam 10, 11, 12. The slight radiation component may involve scattered light 19, for example, which is produced in a small portion on the receiving surface 41 of the radiation sensor 40 if the laser beam 10, 11, 12 impinges on the receiving surface 41. The light sensor 56 can be positioned in such a manner that the receiving surface 41 lies at least partially in the geometrical optical light detection range of the light sensor 56. The light sensor 56 can, for that purpose, be attached to the support mount 20 or in the casing in the region between the expansion device 30 and the radiation sensor 40.

The signal of the light sensor 56 is approximately proportional to the power of the incident laser beam 10. A photodiode can be used as a light sensor 56, for example. A photodiode has a very short signal rise time and consequently provides signals with a very high temporal resolution. By means of the signal of the light sensor 56, the beginning and the end of a pulse or of an irradiation time period of the laser beam 10 can be recorded very precisely. The power of the laser beam 10 can thereby be determined with still higher precision.

The apparatus can be equipped with an electronic computing unit 60. The electronic computing unit 60 processes the electrical signal 47 of the radiation sensor 40. The electronic computing unit can, if necessary, also process the signals of the second temperature sensor 48, as well as of the light sensor 56, if these are provided. The processing of the signals can, for example, include AID conversion and storage of the signals and/or the computation of the power or the energy of the laser beam 10.

The apparatus can be equipped, furthermore, with a display device 64. The data computed, and thus the power or the energy of the laser beam 10, can be displayed by means of the display device.

The apparatus can also be equipped with an interface 62. By means of the interface 62, the data computed, and thus the power or energy of the laser beam, for example, or the signal recorded, can be transmitted to an external device. Control commands can also be exchanged between the apparatus and an external device through the interface 62. The interface 62 can be an electrical interface with a plug connector, such as a USB interface, for example. The interface 62 can also be a wireless interface that makes a data transmission possible by means of a radio signal, such as a so-called Bluetooth interface, for example.

LIST REFERENCE NUMBERS

10 Laser beam
11 Propagating laser beam with increased angle range
12 Propagating laser beam with reduced angle range
13 Diameter of the laser beam in the area of the expansion device
14 Diameter of the laser beam on the receiving surface
16 Virtual course of the laser beam without expansion device
17 Diameter of the virtual laser beam without expansion device
19 Scattered light
20 Support mount
25 Distance between expansion device and radiation sensor
26 Distance between expansion device and collimation device
27 Distance between collimation device and radiation sensor
30 Expansion device
31 Light-scattering structure
33 Beam guiding device
36 Collimation device
37 Converging lens
39 Optical axis of expansion device and radiation sensor
40 Radiation sensor
41 Receiving surface
42 Part of the receiving surface
44 Absorption body
46 Temperature sensor
47 Electrical signal
48 Second temperature sensor
56 Light sensor
60 Electronic computing unit
62 Interface
64 Display device
70 Cooling device
72 Coolant inlet
74 Coolant outlet
77 Coolant

The invention claimed is:

1. Apparatus for the measurement of the power and/or of the energy of a laser beam, comprising a radiation sensor, an expansion device, and a support mount, wherein the radiation sensor has a receiving surface and is configured for the generation of an electrical signal, which is dependent on the power of the laser beam or the energy of the laser beam, wherein the radiation sensor comprises an absorption body and a temperature sensor, and wherein the temperature sensor is thermally coupled with the absorption body, the temperature sensor being adapted to measure a temperature of the absorption body and to generate the electrical signal, wherein the expansion device and the radiation sensor are positioned at a distance from one another on the support mount for the formation of a propagating laser beam between the expansion device and the radiation sensor, wherein the expansion device comprises a lenslet array defined by a plurality of lenslets that are all arranged in a common plane, where the lenslet array is configured in such a way as to increase the angle range of the laser beam, wherein a diameter of the laser beam propagated on the receiving surface is greater than a diameter of the laser beam in the area of the expansion device, and wherein the receiving surface of the radiation sensor encloses at least 90% of the cross-section surface of the laser beam propagated.

2. Apparatus according to claim 1, wherein the common plane of the lenslet array is transverse to an optical axis of the laser beam.

3. Apparatus according to claim 1, wherein the surfaces of the lenslets are curved convexly or concavely.

4. Apparatus according to claim 1, wherein the support mount is configured as a casing, which encloses the expansion device and the radiation sensor and has an opening toward the expansion device.

5. Apparatus according to claim 1, wherein the radiation sensor is configured in such a way that an intensity locally varying within a cross-section of the laser beam is measured as an integral value.

6. Apparatus according to claim 1, wherein the radiation sensor is a large-area photodiode, a large-area semiconductor sensor, a pyroelectrical detector, a thermopile, or a pyrometer.

7. Apparatus according to claim 1, additionally comprising a light sensor, which is configured to measure a slight portion of the laser beam or a scattered light portion of the laser beam.

8. Apparatus according to claim 1, wherein a collimation device is positioned between the expansion device and the radiation sensor.

9. Apparatus according to claim 8, wherein the collimation device comprises a converging lens, an optics consisting of several lenses, a Fresnel lens, a gradient index lens, or a concave mirror.

10. Apparatus according to claim 1, wherein a beam guiding device is positioned between the expansion device and the radiation sensor.

11. Apparatus according to claim 10, wherein the beam guiding device is a light-conducting prism, and inner cylinder mirror, an inner cone mirror, or a kaleidoscope-like mirror arrangement.

12. Method for the measurement of the power and/or of the energy of a laser beam, comprising the following method steps:
  increasing the angle range of the laser beam by means of an expansion device that comprises a lenslet array defined by a plurality of lenslets that are all arranged in a common plane,
  propagation of the laser beam from the expansion device to a radiation sensor with a receiving surface, wherein the expansion device and the radiation sensor are positioned at a distance from one another on a support mount,
  measuring of at least 90% of the cross-section surface of the laser beam propagated by means of the receiving surface of the radiation sensor, wherein a diameter of the laser beam propagated of the receiving surface is greater than a diameter of the laser beam in the area of the expansion device,
  generating an electrical signature by means of the radiation sensor in dependence on the power of the laser beam or the energy of the laser beam, wherein the radiation sensor comprises an absorption body and a temperature sensor, and wherein the temperature sensor is thermally coupled with the absorption body, the temperature sensor measuring a temperature of the absorption body and generating the electrical signal.

13. Method according to claim 12, wherein the increasing of the angle range of the laser beam is carried out by means of using lenslets that have surfaces that are curved convexly or concavely.

14. Method according to claim 12, wherein an intensity locally varying within a cross-section of the laser beam is measured as an integral value.

15. Method according to claim 12, wherein the radiation sensor comprises an absorption body and a temperature sensor, wherein the measuring of at least 90% of the cross-section surface of the laser beam is carried out by means of the receiving surface of the radiation sensor through the absorption of the predominant portion of the laser beam impinging on the receiving surface by means of the absorption body, and wherein the production of the electrical signal is carried out in dependence on the power or the energy of the laser beam through the temperature sensor, which is thermally coupled with the absorption body.

16. Method according to claim 15, additionally comprising the method step:
  determining the energy of the power of the laser beam from the difference between the temperatures of the absorption body after the end of the irradiating of the laser beam and before the beginning of the irradiating of the laser beam.

17. Method according to claim 12, additionally comprising the method step of:
  measuring a slight portion of the laser beam or of a scattered light portion of the laser beam by means of a light sensor.

18. Method according to claim 16, additionally comprising the method steps:
  determining an energy of the laser beam from the difference between the temperatures of the absorption body after the end of the irradiating of the laser beam and before the beginning of the irradiating of the laser beam,
  determining an irradiation period of the laser beam from the course of the signal of the light sensor,
  determining a power of the laser beam through the division of the energy and the irradiation period.

19. Method according to claim 12, wherein the propagation of the laser beam is carried out from the expansion device to the radiation sensor in two sections and the angle range of the propagating laser beam is reduced between the two sections by means of a collimation device, which is position between the expansion device and the radiation sensor.

20. Method according to claim 12, additionally comprising the method step:
  centering of the laser beam propagated on the receiving surface of the radiation sensor by means of a beam guiding device, which is positioned between the expansion device and the radiation sensor.

* * * * *